(12) United States Patent
Lorach et al.

(10) Patent No.: US 8,774,938 B2
(45) Date of Patent: Jul. 8, 2014

(54) IMPLANT HAVING THREE-DIMENSIONAL SHAPE FOR ELECTRICALLY STIMULATING A NERVE STRUCTURE

(75) Inventors: Henri Lorach, Paris (FR); Milan Djilas, Paris (FR); Blaise Yvert, Carignan de Bordeaux (FR); Philippe Bergonzo, Massy (FR); Gaelle Lissorgues, Le Perreux sur Marne (FR); Lionel Rousseau, Le Perreux sur Marne (FR); Ryad Benjamin Benosman, Paris (FR); Serge Picaud, Avon (FR); Jose Sahel, Paris (FR); Siohoi Ieng, Paris (FR)

(73) Assignee: Universite Pierre et Marie Curie (Paris 6), Paris (FR)

( * ) Notice: Subject to any disclaimer, the term of this patent is extended or adjusted under 35 U.S.C. 154(b) by 0 days.

(21) Appl. No.: 13/695,097

(22) PCT Filed: Apr. 29, 2011

(86) PCT No.: PCT/FR2011/050984
§ 371 (c)(1),
(2), (4) Date: Jan. 4, 2013

(87) PCT Pub. No.: WO2011/135273
PCT Pub. Date: Nov. 3, 2011

(65) Prior Publication Data
US 2013/0096660 A1   Apr. 18, 2013

(30) Foreign Application Priority Data

Apr. 30, 2010 (FR) ...................................... 10 53381

(51) Int. Cl.
*A61N 1/00* (2006.01)

(52) U.S. Cl.
USPC .......................................................... 607/116

(58) Field of Classification Search
USPC ........... 607/116, 118, 137; 600/365, 373, 306
See application file for complete search history.

(56) References Cited

U.S. PATENT DOCUMENTS

| 6,112,124 A | 8/2000 | Loeb |
| 8,480,580 B2 * | 7/2013 | Wolpert et al. ............... 600/365 |

(Continued)

FOREIGN PATENT DOCUMENTS

| WO | 2004/073547 A2 | 9/2004 |
| WO | 2009/006636 A2 | 1/2009 |

OTHER PUBLICATIONS

Rousseau, et al., Microfabrication of new microelectrode arrays equipped with a ground surface configuration for focal neural microstimulation, J. Micromech. Microeng., vol. 9 No. 7, 4 pgs. (2009).

(Continued)

*Primary Examiner* — Robert N Wieland
(74) *Attorney, Agent, or Firm* — McAndrews, Held & Malloy Ltd.

(57) ABSTRACT

The invention relates to an implant which includes, in order to electrically stimulate a nerve structure, in particular the retina, an electrically insulating substrate (1), a array of recesses (2) formed in an upper surface of the substrate, stimulation electrodes (3) arranged at the bottom of the recesses, and an electrically conductive layer forming a ground plane (4) at the upper portion of the recesses. The sizes of the recesses and of the electrodes of the implant are such that the spatial selectivity of the stimulation current applied to the nerve structure is maximized.

31 Claims, 3 Drawing Sheets

(56) References Cited

U.S. PATENT DOCUMENTS

| | | | |
|---|---|---|---|
| 2008/0077196 A1 | 3/2008 | Greenberg et al. | |
| 2008/0255439 A1* | 10/2008 | Tang et al. | 600/373 |
| 2010/0036470 A1* | 2/2010 | Nielsen | 607/137 |
| 2010/0305673 A1* | 12/2010 | Jolly et al. | 607/116 |
| 2011/0098796 A1* | 4/2011 | Ben-David et al. | 607/118 |
| 2013/0041235 A1* | 2/2013 | Rogers et al. | 600/306 |
| 2013/0096661 A1* | 4/2013 | Greenberg et al. | 607/116 |
| 2013/0204340 A1* | 8/2013 | Conn et al. | 607/137 |

OTHER PUBLICATIONS

Joucia et al., Improved Focalization of Electrical Microstimulation Using Microelectrode Arrays: A Modeling Study, PLoS One, vol. 4, Issue 3, pp. 13, www.plosone.org, e4828 (Mar. 2009).

Palanker, et al., Migration of Retinal Cells through a Perforated Membrane: Implications for a High-Resolution Prosthesis, IOVAS, vol. 45, No. 9, pp. 3266-3270 Sep. 2004.

Maher, et al., The neurochip: a new multielectrode device for stimulating and recording from cultured neurons, Journal of Neuroscience Methods 87 (1999) 45-56.

PCT International Search Report, International Application No. PCT/FR2011/050984, dated Jul. 21, 2011.

Written Opinion of International Searching Authority and International Preliminary Report on Patentability, International Application No. PCT/FR2011/050984, dated Nov. 6, 2012.

* cited by examiner

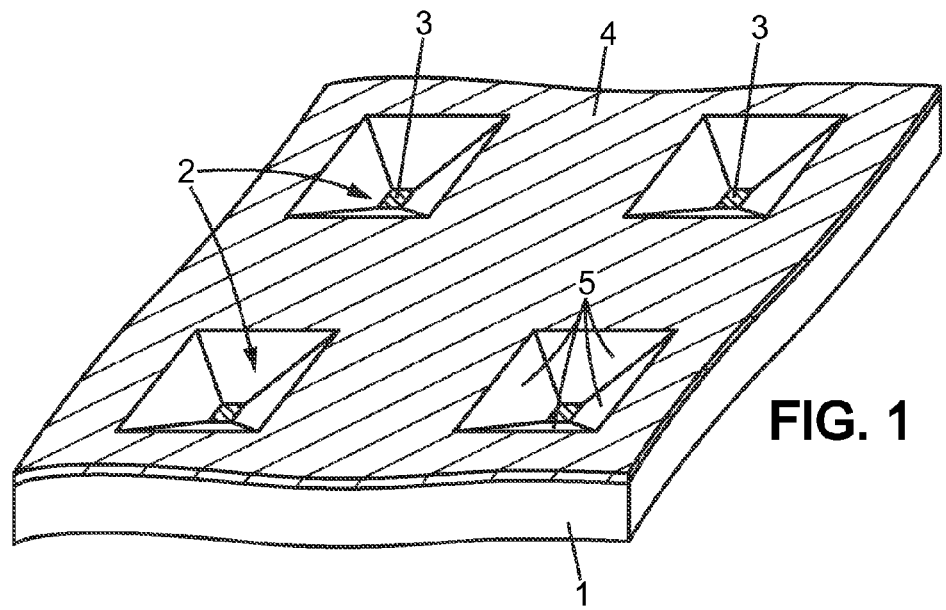
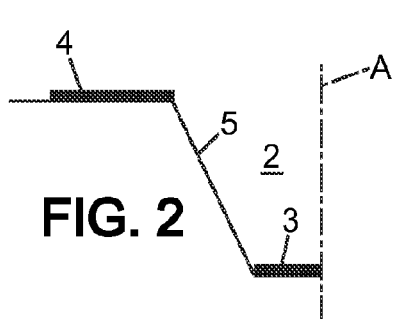
FIG. 2
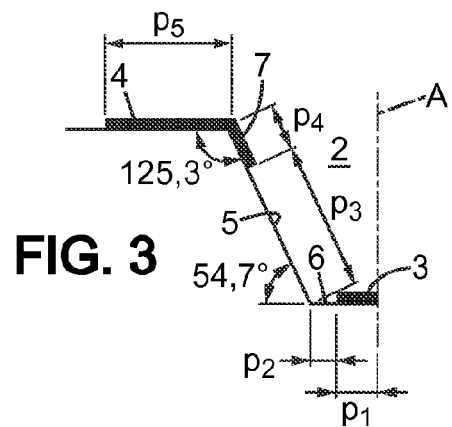
FIG. 3
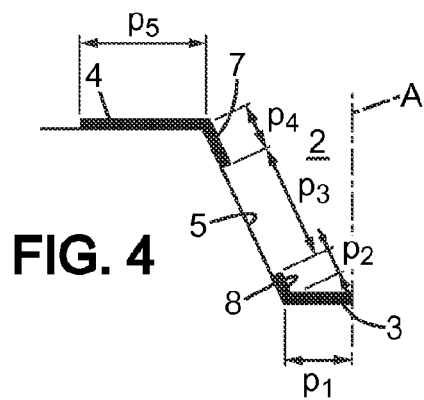
FIG. 4

IMPLANT HAVING THREE-DIMENSIONAL SHAPE FOR ELECTRICALLY STIMULATING A NERVE STRUCTURE

The present application is filed pursuant to 35 U.S.C. 371 as a U.S. National Phase application of International Patent Application No. PCT/FR2011/050984, which was filed Apr. 29, 2011, claiming the benefit of priority to French Patent Application No. 1053381, which was filed on Apr. 30, 2010. The entire text of the aforementioned applications is incorporated herein by reference in its entirety.

This invention relates to implants that can be used to electrically stimulate a nerve structure.

BACKGROUND OF THE INVENTION

For numerous motor or sensory handicaps and pathologies, electrical stimulation of nerve structures has been proposed and even clinically validated. It involves, for example, high-frequency electrical stimulation for the treatment of Parkinson's disease, stimulation of the inner ear for the treatment of deafness, and, more recently, of the retina or the visual cortex for the treatment of blindness. However, a very large number of applications can be envisaged, in particular for sphincter control, the treatment of epilepsy and other neurological diseases.

To implement this type of stimulation, an implant is placed in contact with the nerve structure concerned. Such an implant has electrodes with which an electrical potential difference is applied, or a current is injected, so as to stimulate the nerve cells. A number of electrode configurations have been proposed in order to obtain effective stimulation of the targeted structure.

In the so-called monopolar configuration, current flows between a stimulation electrode and a remote return electrode (at an infinite distance). This monopolar configuration provides stimulation of poor spatial selectivity. However, the spatial selectivity of the electrical stimulation is a desired property in many applications. For example, if the implant has an array of microscopic units juxtaposed so as to perform electrical stimulations independent of one another, in particular to communicate a sharp image to neurons of the retina or the visual cortex, it is important to provide electrical stimulations that are well-localized at each of these units or pixels, with electrical leakage (cross-talk) as low as possible between adjacent pixels.

Bipolar configurations use a pair of electrodes for each area of the nerve structure to be stimulated, excited by positive and negative electrical potentials. The localization of the electrical stimulation is improved with respect to the monopolar configuration, but may still be insufficient for certain applications.

In practice, electrode configurations with a ground plane are preferable to bipolar electrodes since the return electrode is then common to all of the units of the implant, thus dividing the internal wiring of the system by two. In "*Improved Focalization of Electrical Microstimulation Using Microelectrode Arrays: A Modeling Study*" (PLoS ONE, www.plosone.org, Vol. 4, no. 3, e4828, March 2009), S. Joucla and B. Yvert showed improved focusing of the microstimulation with a component of which the surface has a ground plane coplanar with stimulation electrodes.

In "*Migration of retinal cells through a perforated membrane: implications for a high-resolution prosthesis*" (Investigative Ophthalmology & Visual Science, September 2004, Vol. 45, no. 9, pages 3266-3270), D. Palanker et al. studied the capacity of rat retinal cells to migrate thorough an electrically inert perforated membrane, and imagined an implant with a three-dimensional configuration with electrodes projecting over a membrane. However, such an implant appears to be difficult to produce in practice.

In general, it is desirable to produce localized stimulations capable of performing their stimulation role without damaging the tissues. Clinical studies have shown that the current intensities making it possible to obtain a response in the targeted neurons may exceed the safety thresholds for the tissues. Moreover, applications such as vision require the number of electrodes to be multiplied for the same total size of the implant, and therefore to increase their spatial resolution.

There is therefore a need to design electrode structures that make it possible to increase the focusing of the stimulations while limiting the amplitude of the currents generated.

SUMMARY OF THE INVENTION

An implant is proposed for electrical stimulation of a nerve structure including:
  an electrically insulating substrate;
  a array of cavities formed in an upper surface of the substrate;
  stimulation electrodes, each arranged at a bottom portion of one of the cavities; and
  an electrically conductive layer forming a ground plane at an upper portion of the cavities.

The implant will be installed by placing the upper surface of the substrate, fitted with the ground plane, in contact with a tissue comprising nerve cells to be stimulated, which may be located at more or less substantial depths, generally at some tens of microns (μm).

The three-dimensional configuration of the implant with a ground plane makes it possible to focus the electrical stimulation of the target cells inside the cavity. A high spatial selectivity is thus ensured, which makes it possible to obtain a given level of stimulation in the target area with a reduced total current, thereby minimizing damage to the tissues treated. Another advantage of the selectivity obtained is that it enables the number of stimulation units of the implant to be increased while controlling these units independently of one another if required by the application.

In an embodiment of the implant, each cavity has a flared shape that expands from the bottom portion of the cavity toward the upper surface of the substrate. This facilitates the penetration and distribution of the cells in the cavities.

The depth of the cavities is chosen as a function of the depth at which the target cells are supposed to be located in the tissue to be stimulated. Often, a layer of glial cells develops at the interface between the tissue and the electrode, and the neurons located behind this layer are intended to be stimulated. Simulations have shown that, for typical applications, cavities or wells with a depth of more than 15 μm make it possible to have good focusing of the electrical stimulation on the target area.

Cavities with an excessive depth are not desirable either, in particular when their lateral walls are inclined, because this limits the density of cavities on the substrate. It is possible in particular to maintain a cavity depth of less than 50 μm. Cavities with a depth of between 25 and 35 μm appear to be optimal for the compromise between selectivity and size of the cavities.

To limit the size of the cavities, each stimulation electrode may have, on the bottom surface of its respective cavity, a dimension of less than 60 μm.

Other parameters may be adjusted to optimize the performance of the implant. In one configuration, each cavity has an insulating bottom surface partially covered with a stimulation electrode. It is then possible to promote the stimulation of cells relatively close to the surface of the tissue to be treated.

In another configuration, each stimulation electrode has a central part extending over a bottom surface of its respective cavity and a peripheral part overlapping the lateral walls of said cavity. The central part of the stimulation electrode advantageously has a dimension (diameter or side) of less than 40 μm, enabling the focusing of the electrical stimulation to be maximized.

Another possibility is to adjust the shape of the electrically conductive layer forming the ground plane. It is possible in particular to shape it so that it comprises, for each cavity of the array, a part overlapping the lateral walls of said cavity.

BRIEF DESCRIPTION OF THE DRAWINGS

Other features and advantages of the invention will appear in the following description of non-limiting embodiments, in reference to the appended drawings, in which:

FIG. 1 is a perspective diagram of an example of an implant according to the invention;

FIG. 2 is a diagrammatic cross-section view of a cavity of the implant of FIG. 1;

FIGS. 3 and 4 are views similar to that of FIG. 2 concerning other possible embodiments of a cavity of the implant;

DESCRIPTION OF EMBODIMENTS

Figure 5:
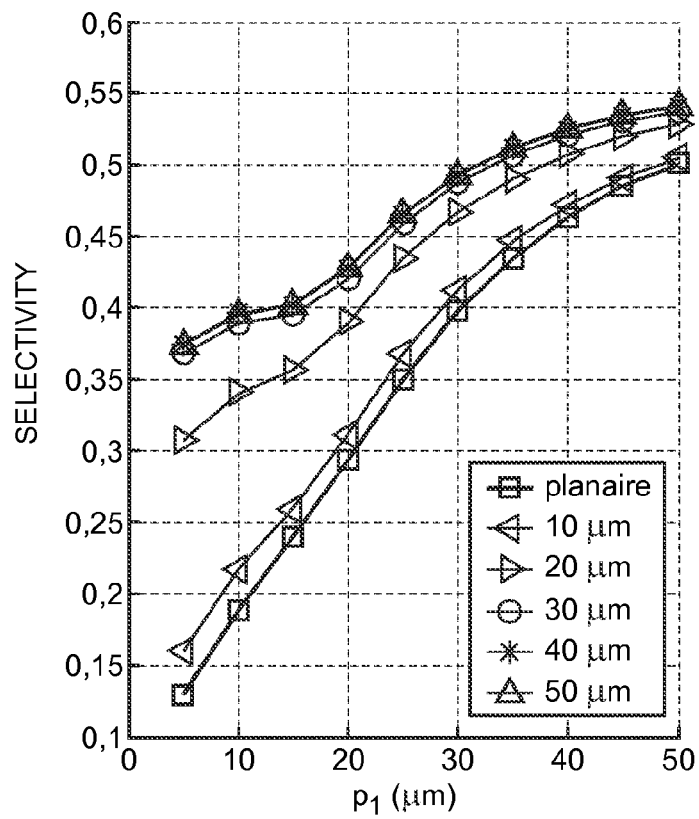
FIGS. 5 and 6 are graphs showing results obtained by simulating the behavior of cavities according to FIGS. 3 and 4, respectively, with different dimensional parameter values.

An exemplary embodiment of an implant according to the invention is shown in FIGS. 1 and 2. It includes an electrically insulating substrate 1 of which the upper surface has an array of cavities 2. A stimulation electrode 3 is located at the bottom portion of each cavity 2.

A return electrode 4 common to the different cavities, or ground plane, is formed by an electrically conductive layer, which, in the example of FIGS. 1 and 2, covers substantially the entire upper surface of the substrate 1 outside of the cavities 2. Between this conductive layer 4 and the stimulation electrodes 3, the cavities 2 have a lateral wall 5 devoid of electrically conductive material.

The application of a potential difference, or the injection of a current, between a stimulation electrode 3 and the ground plane 4 causes propagation of the current in the medium located inside the cavity 2. The cavities 2 and the electrodes 3, 4 can be sized so as to focus the electric field, or the current density, in the cavities 2 by minimizing its propagation in the surrounding medium.

In the example of FIGS. 1 and 2, the cavities 2 have a general reverse-pyramid shape with a truncated apex. Each cavity 2 thus has a flat bottom portion parallel to the upper surface of the substrate 1. This flat bottom portion is entirely covered by the stimulation electrode 3 in this example.

Cavities with different shapes and profiles may also be envisaged, by modifying the design of the starting structure, for example round, triangular, hexagonal, octagonal, etc.

Other electrode configurations, in which the general geometry of the cavity remains similar to that of FIGS. 1 and 2, are shown in FIGS. 3 and 4.

In the case of FIG. 3, the stimulation electrode 3 does not cover the entire bottom portion of the cavity 2. It is surrounded by an insulating margin 6 between the edges of the stimulation electrode 3 and the lateral wall 5 of the cavity. The distance between the axis of symmetry A of the cavity and the edge of the stimulation electrode 3 is denoted as $p_1$, and the distance between the edge of the stimulation electrode 3 and the lateral wall 5 of the cavity 2 is denoted as $p_2$. The stimulation electrode 3 therefore has a size of $2 \times p_1$ along two perpendicular directions in the plane parallel to the substrate 1, and is surrounded by the insulating ring 6 of width $p_2$. The conductive layer of the ground plane 4 extends partially in the plane of the upper surface of the substrate 1, over a width $p_5$ around each cavity, and overlaps the lateral walls 5 of each cavity, forming, at the upper portion of each wall 5, a conductive strip 7 of width $p_4$. The width of the insulating portion of the lateral wall 5 of the cavity 2, between the lower end of the conductive strip 7 and the bottom portion of the cavity 2, is denoted as $p_3$.

In the case of FIG. 4, the ground plane 4 is shown, as in the case of FIG. 3, with the aforementioned dimensional parameters $p_4$ and $p_5$. However, the stimulation electrode 3 covers the entire bottom portion of the cavity 2, of dimension $2 \times p_1$, and in a peripheral part overlaps the lateral walls 5 of the cavity 2. This peripheral part 8 has, along the wall 5, a width denoted $p_2$ in this case. The width $p_3$ of the insulating portion of the lateral wall 5 of the cavity 2 is then measured between the lower end of the conductive strip 7 and the upper end of the peripheral part 8 of the stimulation electrode 3. The example illustrated in FIGS. 1 and 2 is an limit case of FIG. 3 or 4, where $p_2 = p_4 = 0$.

The implant is intended to be applied in vivo against a nerve tissue, with its upper surface covered with the ground plane 4 opposite the tissue. The fact that the cavities 2 have a flared shape expanding from the bottom portion of the cavity toward the upper surface of the substrate 1 facilitates the penetration of the nerve cells into such cavities. As an example, the lateral walls 5, which transversally define a cavity 2, form an angle of 125.3° with the plane of the upper surface of the substrate 1. In other words, the angle of inclination of the lateral wall 5 of the cavity 2 is 54.7°, which corresponds to the preferred angle of etching in a crystalline silicon surface of crystallographic orientation (100).

Simulations have been performed with cavities having cross-sections according to FIGS. 3 and 4, considering the cavities 2 to have a shape with rotational symmetry about their axis A. The physical model used in the simulations was a two-dimensional model with rotational symmetry of a conductive medium with direct currents, defined by the Maxwell equations:

$$J = \sigma . E$$

$$\nabla J = Q$$

$$Q = -\nabla V(\sigma . \nabla V),$$

where J is the current density vector, E is the electrical field vector, σ is the electrical conductivity of the medium, Q is the electrical charge and V is the electrical potential.

In these simulations, the following boundary conditions were imposed by the characteristics of the materials and of the stimulation. For the segments (seen in cross-section) forming the stimulation electrode 3, the flow of the current was toward the inside with a current density corresponding to the intensity, set at 10 μA, divided by the total area of the stimulation electrode. So as not to overestimate the selectivity, the return electrode (or ground plane) was not modeled as an ideal ground plane, but as a distributed resistance at zero potential (conductivity of 338 S/m). Aside from these conductive parts, the other parts of the model were defined as electrical insulators. The current density distributions were calculated in a rectangular domain D=[0,0]×[300 μm, 600 μm]. The electrical resistivity of this domain was set at 50 Ω.m (approximation of the resistivity of the remaining layers in a degenerated retina, of which the photoreceptors are no longer functional).

The electrode geometries were optimized so as to find the optimal parameters for the model that provide the best selectivity of the stimulation. An electrode geometry was considered to be optimal if its set of parameters produced the strongest current concentration in a target area defined as a rectangle T=half-width [from 0 to 20 μm]×height in the cavity [from 20 μm to 40 μm]. The dimensions of this target area were chosen so as to correspond approximately to the location of the functional target cells, taking into account a thin insulating layer of fibrous tissue between the electrodes and the retinal tissue.

The selectivity was quantified in these simulations by dividing the surface integral of the current density distribution in the target area by the surface integral of the current density distribution outside of this target area. For comparative purposes, the optimization was also performed in the case of a planar structure (similar to the configuration of FIG. 3, but with $p_3=p_4=0$.

The ranges of the parameters and their incrementation steps between the iterations used in the optimization are indicated in Table I, in which the values relating to the horizontal segments ($p_1$, $p_2$ and $p_5$ in the case of FIG. 3; $p_1$ and $p_5$ in the case of FIG. 4) represent the segment lengths, while the values relating to the inclined segments ($p_3$ and $p_4$ in the case of FIG. 3; $p_2$, $p_3$ and $p_4$ in the case of FIG. 4) represent the lengths of their projections along axis A. The optimization was performed under the additional constraints that (1) the openings of the manufacturing masks corresponding to the active electrode surfaces must be mutually spaced apart by at least 5 μm and (2) the cavity depth does not exceed 50 μm.

TABLE I

| | | $p_1$ [μm] | $p_2$ [μm] | $p_3$ [μm] | $p_4$ [μm] | $p_5$ [μm] |
|---|---|---|---|---|---|---|
| Planar | Initial value | 5 | 5 | 0 | 0 | 5 |
| | Step | 5 | 5 | — | — | 5 |
| | Final value | 50 | 50 | — | — | 30 |
| FIG. 3 | Initial value | 5 | 0 | 0 | 0 | 5 |
| | Step | 5 | 2 | 2 | 2 | 5 |
| | Final value | 50 | 10 | 50 | 50 | 30 |
| FIG. 4 | Initial value | 0 | 0 | 0 | 0 | 5 |
| | Step | 5 | 2 | 2 | 2 | 5 |
| | Final value | 50 | 50 | 50 | 50 | 30 |

For the specific cases of the geometries in FIGS. 3 and 4, the optimal parameters as a function of cavity depth are summarized in Table II. In the case of FIG. 3, the cavity depth is the sum of the projections on axis A of the parameters $p_3$ and $p_4$, while in the case of FIG. 4, it is the sum of the projections on axis A of parameters $p_2$, $p_3$ and $p_4$. The selectivity of the electrodes as a function of the parameter $p_1$ representing the half-dimension of the stimulation electrode 3 and of the depth of the cavity 2 is shown in FIG. 5 for the electrode configuration of FIG. 3 and in FIG. 6 for the electrode configuration of FIG. 4. In these FIGS. 5 and 6, each point was obtained by finding the optimal values for parameters $p_2$, $p_3$, $p_4$ and $p_5$ for given values of $p_1$ and the cavity depth.

TABLE II

| | Cavity depth [μm] | $p_1$ [μm] | $p_2$ [μm] | $p_3$ [μm] | $p_4$ [μm] | $p_5$ [μm] | Selectivity |
|---|---|---|---|---|---|---|---|
| FIG. 3 | 10 | 50 | 0 | 7 | 0 | 30 | 0.50 |
| | 20 | 50 | 0 | 14 | 0 | 30 | 0.53 |
| | 30 | 50 | 0 | 21 | 0 | 30 | 0.54 |
| | 40 | 50 | 0 | 28 | 0 | 10 | 0.54 |
| | 50 | 50 | 0 | 31 | 4 | 5 | 0.54 |
| FIG. 4 | 10 | 50 | 1 | 6 | 0 | 30 | 0.51 |
| | 20 | 0 | 9 | 6 | 0 | 30 | 0.69 |
| | 30 | 0 | 16 | 6 | 0 | 5 | 1.65 |
| | 40 | 0 | 18 | 6 | 4 | 5 | 1.62 |
| | 50 | 0 | 18 | 7 | 10 | 5 | 1.47 |

In the configuration according to FIG. 3, selectivity increases with parameter $p_1$, while it decreases in the configuration according to FIG. 4. In both cases, the selectivity is improved when the cavity 2 becomes deeper. For a cavity depth of less than 20 μm (lower edge of the target area), there is little difference between the two configurations, and with the planar configuration, even if a certain improvement is already noted for a depth of 10 μm. A value of 15 μm can be used as a minimum value for the depth in the design of an implant.

For greater depths, the configuration of FIG. 4 provides the best results, but already a substantial improvement is observed with the configuration of FIG. 3 with respect to the planar case. For each three-dimensional configuration of the electrodes, the selectivity reaches its maximum for a depth on the order of 30 μm. However, no substantial degradation in selectivity is observed when the depth increases to 50 μm. The compromise between selectivity and bulk is most satisfactory for cavity depths between 25 and 35 μm.

The optimal parameters of the configuration of FIG. 4 provide the best selectivity for the smallest stimulation electrode sizes. Thus, for an electrode of diameter 10 μm ($p_1=5$ μm), there is, with respect to the planar configuration, an increase in selectivity on the order of three for the configuration of FIG. 3 and on the order of ten for that of FIG. 4.

Figure 6:
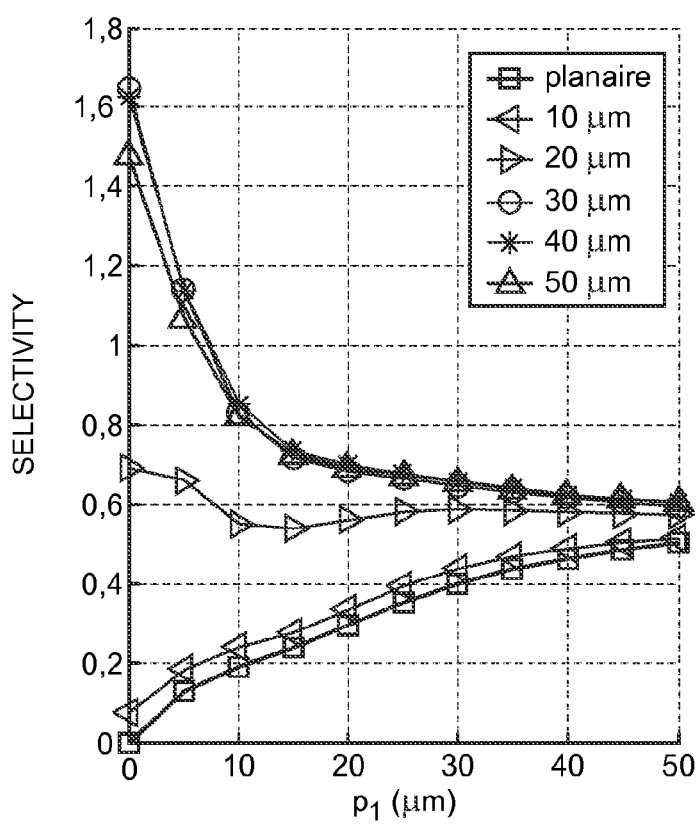

In general, a stimulation electrode 3 with a dimension of less than 60 μm on the bottom surface of the cavity 2 (i.e. $p_1<30$ μm) has the advantage of providing relatively compact cavities 2, therefore capable of being produced with a relatively high density on the substrate. In the case of FIG. 4, in which the stimulation electrode 3, in its peripheral part 8, overlaps the lateral wall of the cavity, the very small stimulation electrode sizes 3 (less than 40 μm, i.e. $p_1<20$ μm) also have the remarkable advantage of leading to very high selectivity values as shown in FIG. 6.

To combine as many electrodes as possible in an array, the smallest possible parameters $p_1$ and $p_5$ should be taken, because this results in a minimal electrode size and therefore the smallest inter-electrode distance. The effect of a disturbance of these two parameters $p_1$ and $p_5$ was studied and is summarized in FIGS. 7 and 8. For this, the parameter $p_1$ was varied in the range indicated in Table I while maintaining the four other parameters at their optimal values found for a cavity depth of 30 μm. The same procedure was repeated for parameter $p_5$.

Figure 7:
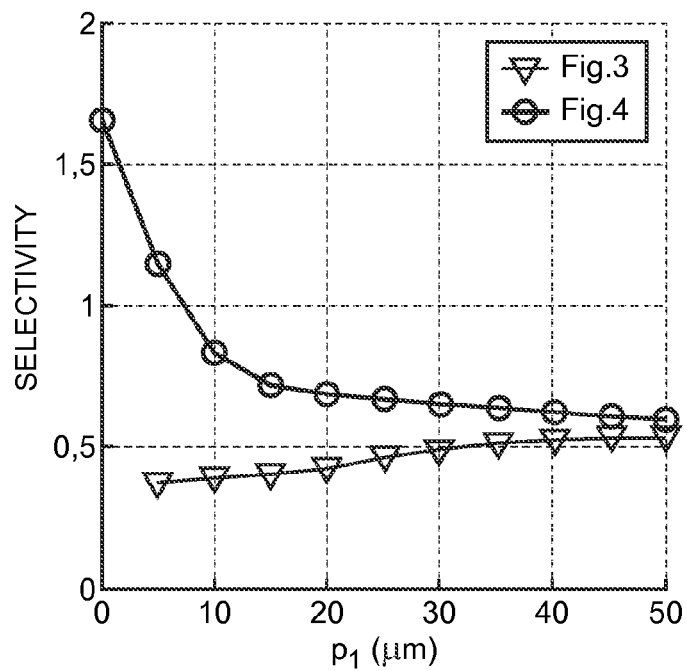
FIGS. 7 and 8 are graphs showing the effect of a disturbance of certain parameters on the simulation results shown in FIGS. 5 and 6.
Figure 8:
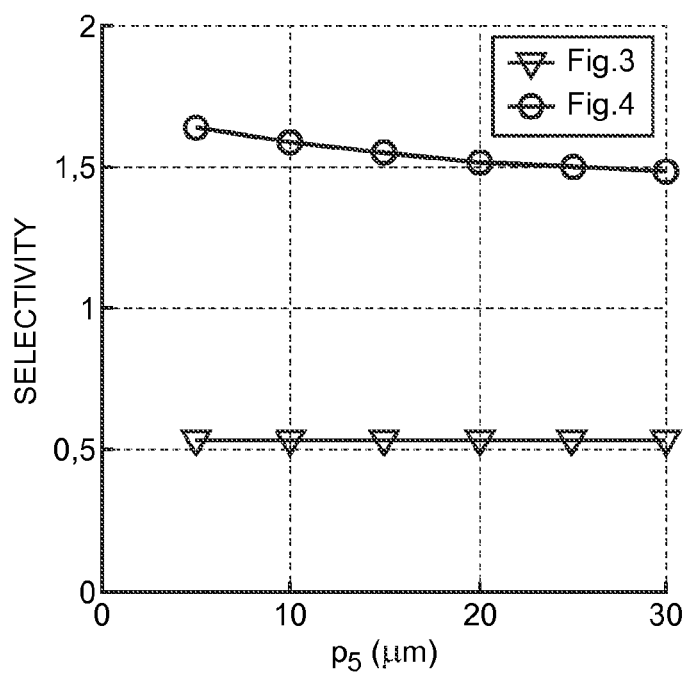

As shown in FIG. 7, changing the size of the stimulation electrode in the configuration of FIG. 3 has relatively little influence on selectivity. However, the selectivity is degraded when $p_1$ increases in the configuration of FIG. 4. In this last case, it is therefore beneficial to choose $p_1$ so as to be as small as possible, making sure that the current densities produced remain within a safety limit for the electrode material. Platinum may deliver 0.35 to 0.40 mC/cm$^2$ without problems while iridium oxide has a safe stimulation limit of up to 3 to 4 mC/cm$^2$. The small stimulation electrode sizes also have an advantage in terms of reduction of the activation threshold of the cells. However, a potential problem if the value of $p_1$ becomes too small is that the cavity may become too narrow. A retinal bipolar cell has a size on the order of 10 μm, so the retinal tissue to be stimulated may not penetrate the cavity 2 if it becomes too small.

The little effect on selectivity of a perturbation of parameter $p_5$ (FIG. 8) means that the stimulation current still remains well confined within the cavity. A very limited extension of the return electrode on the upper surface of the substrate 1 is enough to eliminate inter-electrode current leakage (cross-talk). The cavities 2 can therefore be combined on the substrate 1 almost edge-to-edge. In combination with the choice of a small value of $p_1$, this makes it possible to design high-density electrodes. The maximum number of electrodes is finally restricted by the capacity to implant conductive tracks to supply power to them, as these tracks have a minimum width to be taken into consideration.

The simulations reported above show that the three-dimensional electrode structures proposed improve the focusing of the simulation in an implant intended for the retina or other nerve structures belonging to the central nervous system or the peripheral nervous system.

The technologies of the silicon industry can be used to produce an implant having the above characteristics. A monocrystalline silicon wafer is then used as a mold. Truncated pyramids for example are formed on a surface (100) of this wafer by a wet etching process through a mask having patterns reproducing the shape of the cavity bases. The etching is preferably performed according to the plans (111), which leaves the angle of 54.7° for the lateral walls 5 as mentioned above, with kinks that may present near the angles of the pyramids. A conductive layer, for example of platinum or iridium oxide, is deposited through a photoresist mask of a suitable shape so as to produce the ground plane 4 and the stimulation electrodes 3 at the bottom portions of the cavities 2 (i.e. at the apex of the truncated pyramids). A resin of a biocompatible polymer, for example a polyimide or a parylene, is deposited on the structure so as to cover the pyramids, and it is polymerized to form the substrate 1. The connections of the electrodes are produced on this substrate, then the silicon is removed (for example, by oxidation then chemical etching) so as to obtain the implant of which the upper surface is covered with the ground plane 4 and has the cavities 2 with the desired shapes and sizes.

The silicon technologies also provide the advantage of making it possible to produce isotropic-type etchings, either by plasma or liquid etching. This makes it possible to obtain a wide enough range of shapes for the cavities. Starting with a circle pattern, it is possible to obtain a truncated cone-shaped cavity. Starting with a triangular pattern, it is possible to obtain a truncated pyramid-shaped cavity, etc. These etching techniques also make it possible to adjust the angle of the cavity walls if desired.

It should be understood that the invention is not limited to the specific embodiments described above or to any manufacturing method. Various alternatives may be designed without going beyond the scope defined by the appended claims.

The invention claimed is:

1. Implant for electrical stimulation of a nerve structure comprising:
    an electrically insulating substrate;
    an array of cavities formed in an upper surface of the substrate, each cavity having a flared shape that expands from a bottom portion of said cavity toward the upper surface of the substrate;
    stimulation electrodes, each arranged at the bottom portion of one of the cavities; and
    an electrically conductive layer forming a ground plane at an upper portion of the cavities.

2. Implant according to claim 1, wherein the cavities have a depth greater than 15 μm.

3. Implant according to claim 1, wherein the cavities have a depth lower than 50 μm.

4. Implant according to claim 1, wherein the cavities have a depth of between 25 and 35 μm.

5. Implant according to claim 1, wherein each stimulation electrode has, on a bottom surface of its respective cavity, a dimension of less than 60 μm.

6. Implant according to claim 1, wherein each cavity has an insulating bottom surface partially covered with a stimulation electrode.

7. Implant according to claim 1, wherein each stimulation electrode has a central part extending over a bottom surface of its respective cavity and a peripheral part overlapping lateral walls of said cavity.

8. Implant according to claim 7, wherein said central part of the stimulation electrode has a dimension of less than 40 μm.

9. Implant according to claim 1, wherein the electrically conductive layer forming the ground plane comprises, for each cavity of the array, a part overlapping lateral walls of said cavity.

10. An implant for electrical stimulation of a nerve structure comprising:
    an electrically insulating substrate;
    an array of cavities formed in an upper surface of the substrate, the cavities having a depth greater than 15 μm;
    stimulation electrodes, each arranged at a bottom portion of one of the cavities; and
    an electrically conductive layer forming a ground plane at an upper portion of the cavities.

11. Implant according to claim 10, wherein the cavities have a depth lower than 50 μm.

12. Implant according to claim 10, wherein the cavities have a depth of between 25 and 35 μm.

13. Implant according to claim 10, wherein each stimulation electrode has, on a bottom surface of its respective cavity, a dimension of less than 60 μm.

14. Implant according to claim 10, wherein each cavity has an insulating bottom surface partially covered with a stimulation electrode.

15. Implant according to claim 10, wherein each stimulation electrode has a central part extending over a bottom surface of its respective cavity and a peripheral part overlapping lateral walls of said cavity.

16. Implant according to claim 15, wherein said central part of the stimulation electrode has a dimension of less than 40 μm.

17. Implant according to claim 10, wherein the electrically conductive layer forming the ground plane comprises, for each cavity of the array, a part overlapping lateral walls of said cavity.

18. Implant for electrical stimulation of a nerve structure comprising:
- an electrically insulating substrate;
- an array of cavities formed in an upper surface of the substrate, the cavities having a depth lower than 50 μm;
- stimulation electrodes, each arranged at a bottom portion of one of the cavities; and
- an electrically conductive layer forming a ground plane at an upper portion of the cavities.

19. Implant according to claim 18, wherein each stimulation electrode has, on a bottom surface of its respective cavity, a dimension of less than 60 μm.

20. Implant according to claim 18, wherein each cavity has an insulating bottom surface partially covered with a stimulation electrode.

21. Implant according to claim 18, wherein each stimulation electrode has a central part extending over a bottom surface of its respective cavity and a peripheral part overlapping lateral walls of said cavity.

22. Implant according to claim 21, wherein said central part of the stimulation electrode has a dimension of less than 40 μm.

23. Implant according to claim 18, wherein the electrically conductive layer forming the ground plane comprises, for each cavity of the array, a part overlapping lateral walls of said cavity.

24. Implant for electrical stimulation of a nerve structure comprising:
- an electrically insulating substrate;
- an array of cavities formed in an upper surface of the substrate;
- stimulation electrodes, each arranged at a bottom portion of one of the cavities and having, on a bottom surface of said one of the cavities, a dimension of less than 60 μm; and
- an electrically conductive layer forming a ground plane at an upper portion of the cavities.

25. Implant according to claim 24, wherein each cavity has an insulating bottom surface partially covered with a stimulation electrode.

26. Implant according to claim 24, wherein each stimulation electrode has a central part extending over a bottom surface of its respective cavity and a peripheral part overlapping lateral walls of said cavity.

27. Implant according to claim 26, wherein said central part of the stimulation electrode has a dimension of less than 40 μm.

28. Implant according to claim 24, wherein the electrically conductive layer forming the ground plane comprises, for each cavity of the array, a part overlapping lateral walls of said cavity.

29. Implant for electrical stimulation of a nerve structure comprising:
- an electrically insulating substrate;
- an array of cavities formed in an upper surface of the substrate;
- stimulation electrodes, each arranged at a bottom portion of one of the cavities and having a central part extending over a bottom surface of said one of the cavities and a peripheral part overlapping lateral walls of said one of the cavities, said central part having a dimension of less than 40 μm; and
- an electrically conductive layer forming a ground plane at an upper portion of the cavities.

30. Implant according to claim 29, wherein the electrically conductive layer forming the ground plane comprises, for each cavity of the array, a part overlapping the lateral walls of said cavity.

31. Implant for electrical stimulation of a nerve structure comprising:
- an electrically insulating substrate;
- an array of cavities formed in an upper surface of the substrate;
- stimulation electrodes, each arranged at a bottom portion of one of the cavities; and
- an electrically conductive layer forming a ground plane at an upper portion of the cavities and comprising, for each cavity of the array, a part overlapping lateral walls of said cavity.

* * * * *